(12) United States Patent
Chen et al.

(10) Patent No.: US 7,567,079 B2
(45) Date of Patent: Jul. 28, 2009

(54) METHODS SUITABLE FOR MEASURING CAPILLARY PRESSURE AND RELATIVE PERMEABILITY CURVES OF POROUS ROCKS

(75) Inventors: Quan Chen, Sunbury on Thames (GB); Bruce J. Balcom, Fradenedton (CA)

(73) Assignee: University of New Brunswick, Fredericton (CA)

( * ) Notice: Subject to any disclaimer, the term of this patent is extended or adjusted under 35 U.S.C. 154(b) by 97 days.

(21) Appl. No.: 11/808,300

(22) Filed: Jun. 8, 2007

(65) Prior Publication Data

US 2008/0303520 A1 Dec. 11, 2008

(51) Int. Cl.
*G01V 3/00* (2006.01)
(52) U.S. Cl. .................................. 324/303; 324/306
(58) Field of Classification Search ............. 324/303, 324/306
See application file for complete search history.

(56) References Cited

U.S. PATENT DOCUMENTS

| | | | |
|---|---|---|---|
| 4,769,602 A * | 9/1988 | Vinegar et al. | 324/303 |
| 4,893,504 A | 1/1990 | O'Meara, Jr. et al. | |
| 5,162,733 A | 11/1992 | Baldwin | |
| 5,297,420 A | 3/1994 | Gilliland et al. | |
| 5,493,226 A | 2/1996 | Honarpour et al. | |
| 6,415,649 B1 * | 7/2002 | Spinler et al. | 73/38 |
| 6,497,139 B1 | 12/2002 | Locatelli | |
| 6,512,371 B2 * | 1/2003 | Prammer | 324/303 |
| 6,998,845 B2 | 2/2006 | Martin et al. | |
| 7,092,822 B2 * | 8/2006 | Lenormand et al. | 702/9 |
| 7,352,179 B2 * | 4/2008 | Chen et al. | 324/303 |
| 7,363,161 B2 * | 4/2008 | Georgi et al. | 702/7 |
| 2006/0116828 A1 | 6/2006 | Chen et al. | |
| 2006/0132131 A1 | 6/2006 | Fleury et al. | |

OTHER PUBLICATIONS

Dullien F., Porous Media: fluid transport and pore structure, 2nd Edition, Academic Press, New York (1991), p. 138-176.
Bear J., Dynamics of Fluids In Porous Media, Dover Publications Inc., New York (1972), p. 444.
Balcom B., J. Barrita, C. Choi, S. Beyea, D. Goodyear, and T. Bremner, Single-point magnetic resonance imaging (MRI) of cement based materials, Materials and Structures vol. 36, p. 166-182 (2003).

(Continued)

*Primary Examiner*—Louis M Arana
(74) *Attorney, Agent, or Firm*—Eugene Derényi

(57) ABSTRACT

Single-shot methods suitable for determining capillary pressure and relative permeability curves in petroleum reservoir core plugs are proposed. Three classes of measurement are outlined. (i) Measurements undertaken with steady state gas flow and stationary water or oil phases in the rock. SPRITE (Single-Point Ramped Imaging with $T_1$ Enhancement) MRI (Magnetic Resonance Imaging) spin density images map spatially varying fluid content. (ii) Similar measurements are proposed with a stationary gas phase and flowing water or oil phases. (iii) Measurements are also possible with either water or oil as the stationary phase, with the other phase undergoing steady state flow. In all cases the outflow boundary condition is maintained, capillary pressure zero, by washing the outlet face of the sample with the stationary fluid phase.

64 Claims, 4 Drawing Sheets

OTHER PUBLICATIONS

Balcom, B, R. MacGregor, S. Beyea, D. Green, R. Armstrong, T. Bremner, Single Point Ramped Imaging with T1 Enhancement (SPRITE), J. Magn, Reson., Series A, vol. 123, p. 131-134 (1996).

Chen, Q., M. Halse and B. Balcom, Centric scan SPRITE for spin density imaging of short relaxation time porous materials, Magn, Reson. Imaging 23, p. 263-266 (2005).

Chen, Q., M. Gingras and B. Balcom, A magnetic resonance study of pore filling processes during spontaneous imbibition in Berea sandstone, J. of Chem. Phys. vol. 119, No. 18, p. 9609-9616 (2003).

Chen Q., A. Marble, B. Colpitts and B. Balcom, The internal magnetic field distribution, and single exponential magnetic resonance free induction decay, in rocks, J. Magn. Reson., vol. 175, p. 300-308 (2005).

Mastikhin, I., B. Balcom, P.J. Prado, and C.B. Kennedy, SPRITE MRI with Prepared Magnetization and Centric k-Space Sampling, J. Magn. Reson. vol. 136, p. 159-168 (1999).

M. Bencsik, C. Ramanathan, Direct measurement of porous media local hydrodynamical permeability using gas MRI, Magnetic Resonance Imaging vol. 19 (2001) p. 379-383.

M.C. Leverett, Capillary Behavior in Porous Solids (Manuscript received at the office of the Institute Jun. 14, 1940. Issued as T.P. 1223 in Petroleum Technology, Aug. 1940.).

Harry W. Brown, Capillary Pressure Investigations, Petroleum Transactions, AIME, vol. 192, 1951, p. 67-74.

Norgaard, J.V., D. Olsen, J. Reffstrup, and N. Springer, Capillary Pressure Curves for Low-Permeability Chalk Obtained by Nuclear Magnetic Resonance Imaging of Core-Saturation Profiles, SPE Reservoir Eval. & Eng., vol. 2 (2) (1999).

Fordham, E.J., L.D. Hall, R.S. Ramakrishnan, M.R. Sharpe and C.Hall, Saturation Gradients in Drainage of Porous Media: NMR Imaging Measurements, AlChE Journal, vol. 39, No. 9 (Sep. 1993) p. 1431-1443.

\* cited by examiner

METHODS SUITABLE FOR MEASURING CAPILLARY PRESSURE AND RELATIVE PERMEABILITY CURVES OF POROUS ROCKS

CROSS-REFERENCE TO RELATED APPLICATIONS

This is the first application filed for the present invention.

MICROFICHE APPENDIX

Not applicable

TECHNICAL FIELD

This application relates to techniques for determining basic rock-fluid properties and quantities derived therefrom in multiphase flows in general, and to methods suitable for measuring capillary pressure and relative permeability curves of porous rocks, in particular.

BACKGROUND OF THE INVENTION

Capillary pressure and relative permeability are the most basic rock-fluid properties in multiphase flows. In laboratory, two types of experimental techniques are generally used for determining relative permeability: steady-state and unsteady-state methods. For steady-state methods, the two fluids are injected simultaneously into the porous medium at a fixed ratio until the inflows equal the outflows and a constant pressure drop have been reached. It may take 2 to 40 hours or even longer to reach the steady-state conditions. According to Dullien F., *Porous Media: fluid transport and pore structure*, 2nd Edition, Academic Press, New York (1991), 139-176 and Bear J., *Dynamics of Fluids in Porous Media*, Dover Publications, New York, (1972), 444, which is incorporated herein by reference in its entirety, the relative permeability corresponding to the saturation established during the experiment can be determined by a modified form of Darcy's law:

$$\frac{Q_j}{A} = -\frac{KK_{rj}}{\mu_j}\frac{\Delta P_j}{L} \quad (1)$$

where $Q_j$, $P_j$, $\mu_j$, and $K_{rj}$ are volume flux, pressure, viscosity; and relative permeability of fluid phase j, respectively. A, K, and L are the cross-sectional area, absolute permeability and length of the porous medium, respectively.

The injection ratio is then changed, until a new steady flow is established to calculate the relative permeability corresponding to this saturation. Different approaches may be employed to eliminate the capillary end effects and try to ensure uniform saturation distribution in the whole sample. The steady-state measurements are very time consuming. In addition, the conditions of steady-state and uniform saturation distribution are very rarely reached, and errors are introduced therefrom.

SPRITE MRI

Standard SPRITE MRI

The standard SPRITE MRI technique as taught in Balcom B., J. Barrita, C. Choi, S. Beyea, D. Goodyear and T. Bremner, *Single-point magnetic resonance imaging (MRI) of cement based materials*, Materials and Structures 36, 166 (2003), which is incorporated herein by reference in its entirety, has proven to be a very robust and flexible method for the study of a wide range of systems with short MR relaxation times. As a pure phase encoding technique, SPRITE is largely immune to image distortions due to susceptibility variation, chemical shift, and paramagnetic impurities. Repetitive excitation and data acquisition are performed in the presence of ramped phase encoding gradients, which enable systems with $T_2^*$ lifetimes as short as tens of microseconds to be successfully visualized.

Centric Scan SPRITE MRI

A centric scan strategy for SPRITE MRI as taught in Balcom B., R. MacGregor, S. Beyea, D. Green, R. Armstrong and T. Bremner, *Single Point Ramped Imaging with $T_1$ Enhancement (SPRITE)*, J. Magn. Reson. A 123, 131 (1996) and Mastikhin I., B. Balcom, P. Prado and C. Kennedy, SPRITE MRI with Prepared Magnetization and Centric k Space Sampling, J. Magn. Reson. 136, 159 (1999), which are incorporated herein by reference in their entirety, removes the longitudinal steady state from the image intensity equation of standard SPRITE imaging, and increases the inherent image intensity. The image signal intensity no longer depends on the longitudinal relaxation time and the repetition time. These features ensure that centric scan SPRITE is an ideal method for quantitative imaging of sedimentary rocks with short relaxation times.

SUMMARY

According to one aspect of the present invention, there is provided: a method suitable for at least enabling the measurement of a property of a porous rock, the method comprising the steps of: (a) providing a porous rock core having a length, an inlet face, and an outlet face; (b) saturating the porous rock core with a first fluid; (c) displacing the first fluid by applying a second fluid to the inlet face of the porous rock core; (d) washing the outlet face of the porous rock core with said second fluid so as to maintain an outflow boundary condition; (e) determining that a substantially steady-state condition has been reached where the fluid saturation distribution and pressure distribution along the length of the core do not substantially change with time; (f) performing a fluid saturation distribution measurement of the porous rock core comprising the act of: measuring the local fluid saturation using Nuclear Magnetic Resonance Imaging (NMR) wherein a single exponential free induction decay (FID) rate 1/T2* is used to provide an NMR linewidth $\Delta v$ is substantially equal to $1/\pi T_2^*$; (g) performing a pressure distribution measurement of the porous rock core; and (h) determining a property of the porous rock core by using fluid saturation measurement.

According to another aspect of the present invention, there is provided: a method suitable for determining capillary pressure and relative permeability curves of a porous rock core having an inlet face and an outlet face, the method comprising the steps of: (a) maintaining a steady-state gas flow, with stationary water or oil remaining in a porous rock core; (b) maintaining an outflow boundary condition whereat capillary pressure is zero by washing the outlet face of the core with a stationary phase; (c) measuring a water or oil saturation distribution, S(x), at the present of steady-state flowing gas, using MRI; and (d) determining a gas pressure distribution, P(x), by SPRITE (Single-Point Ramped imaging with T1 Enhancement) MRI (Magnetic Resonance Imaging) spin density imaging of flowing gas, whereby the pressure of the gas phase is directly proportional to the spin density of gas.

Other aspects and features of the present invention will become apparent to those ordinarily skilled in the art upon review of the following description of specific embodiments of methods suitable for measuring capillary pressure and relative permeability curves of porous rocks in conjunction with the accompanying drawing figures.

BRIEF DESCRIPTION OF THE DRAWINGS

Embodiments of the present invention will now be described, by way of example only, with reference to the accompanying drawing figures, wherein.

Like reference numerals are used in different figures to denote similar elements.

DETAILED DESCRIPTION OF THE DRAWINGS

Figure 1:
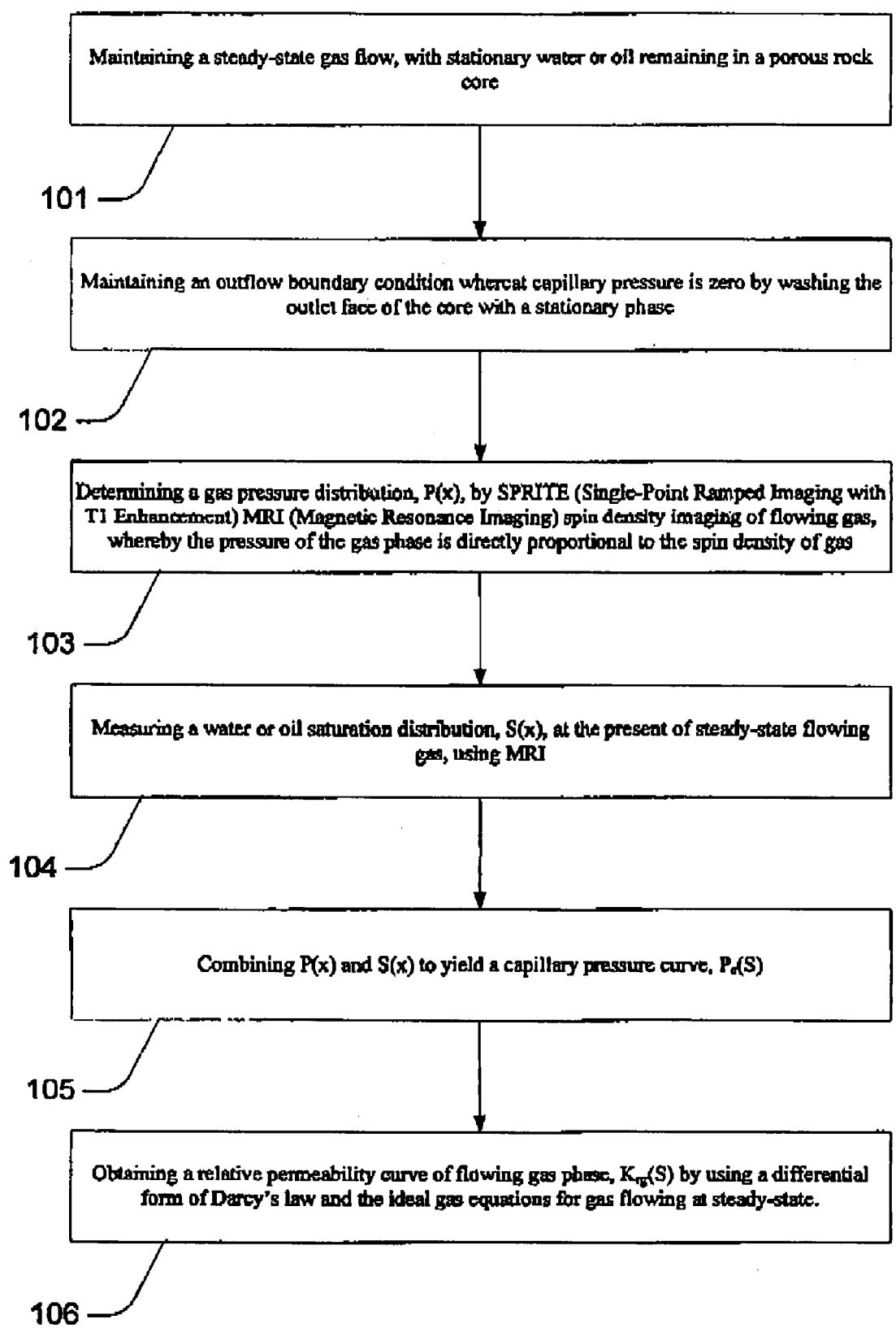
FIG. 1 is a flowchart illustrating steps of one embodiment of a method provided according to the present invention.

Referring to the drawings, FIG. 1 is a flowchart illustrating steps of one embodiment of a method provided according to the present invention. One embodiment of single-shot methods suitable for determining capillary pressure and relative permeability curves is proposed. For steady-state gas flow as per step 101, with stationary water or oil remaining in a porous rock core and the outflow boundary condition (capillary pressure is zero) is maintained by washing the outlet face of the core with the stationary phase as per step 102. In one embodiment, this is achieved by directing a local flow of the phase of interest across the outlet face of the sample, such as by directing a stream of water or oil or gas across the exit end of the sample. The gas pressure distribution, P(x), is determined by SPRITE (Single-Point Ramped Imaging with $T_1$ Enhancement) MRI (Magnetic Resonance Imaging) spin density imaging of flowing gas, since the spin density of gas is directly proportional to the pressure of the gas phase as per step 103. Water or oil saturation distribution, S(x), at the present of steady-state flowing gas, is measured with MRI at step 104. The combination of P(x) and S(x) yields a capillary pressure curve, $P_c(S)$ as per step 105 and relative permeability is curve of flowing gas phase, $K_{rg}(S)$ can be determined with differential form of Darcy's law and ideal gas equations for gas flowing at steady state as per step 106.

In the case that oil or water is flowing phase and gas is stationary phase, the outflow boundary condition is maintained by washing the outlet face of the core with the gas phase, after steady-state condition is reached, the gas phase pressure distribution and flowing water or oil saturation distribution, as well as capillary pressure curve can also be obtained by the similar methods described in the early sections.

For steady-state water or oil flow, with stationary gas remaining in the porous rock core, the outflow boundary condition is maintained by washing the outlet face of the core with the gas phase, after steady-state condition is reached, the gas pressure distribution, P(x), is determined by SPRITE MRI spin density imaging of the stationary gas. Water or oil saturation distribution, S(x), can be measured with SPRITE MRI while water or oil is flowing. The combination of P(x) and S(x) yields a capillary pressure curve, $P_c(S)$ and relative permeability curve of flowing water or oil phase, i.e., $K_{rw}(S)$ or $K_{ro}(S)$ can be determined with differential form of Darcy's law.

For oil and water system, the capillary pressure curve, $P_c(S)$, of the core can be determined by a single-shot centrifuge and MRI method. After the single-shot centrifuge experiment, the core is put into a nonmagnetic core holder for steady-state flow experiment, the outflow boundary condition is maintained by washing the outlet face of the core with the stationary phase. After the steady-state is reached, water and oil saturation distributions, S(x), along the length of the core can be obtained be SPRITE MRI. A combination of $P_c(S)$ and S(x) yields a capillary distribution along the length of the core, $P_c(x)$. The $P_c(x)$ can be used to determine the flowing phase relative permeability with differential form of Darcy's law.

The single-shot methods require the stationary phase to reach irreducible fluid saturation at inlet face. The inlet pressure for the single-shot methods can be determined by Leverret J function at irreducible fluid saturation.

Centric Scan SPRITE MRI

Figure 2:
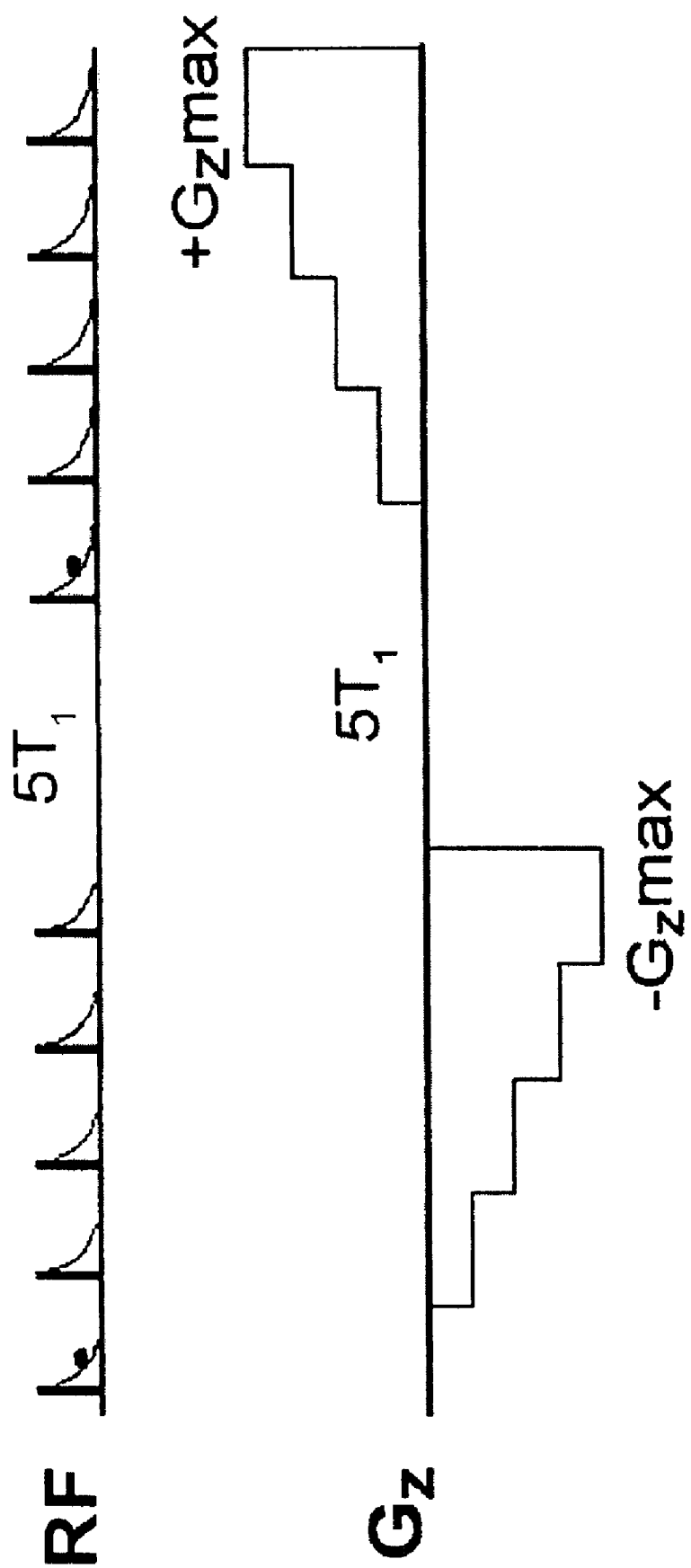
FIG. 2 is a graph illustrating a 1D centric scan SPRITE, MRI technique

Referring to the drawings, FIG. 2 is a graph illustrating a 1D centric scan SPRITE MRI technique, where the k-space data are acquired sequentially from '0' to '$-k_z$', corresponding to a gradient change from 0 to minus maximum gradient (−Gmax). According to this double half k-space acquisition strategy, after a delay of 5 times $T_1$, the other of half k-space data is collecting from '0' to '$+k_z$', corresponding to a gradient change from 0 to a maximum gradient (Gmax). Fourier transformation of the k-space data yields a real space image. In the centric scan SPRITE technique, the image signal intensity (S) is given by:

$$S(r) = M_0(r)\exp\left(-\frac{t_p}{T_2^*}\right)\sin\alpha \quad (2)$$

Where $M_0$ is the equilibrium magnetization, $\alpha$ is the RF flip angle, $t_p$ is the phase encoding time, $T_2^*$ is the effective transverse relaxation time. $M_o$ is directly proportional to the local fluid content. Centric scan SPRITE techniques are naturally fluid content weighted.

Spin Density Imaging with SPRITE MRI

A wide range of experimental results published in Chen, Q., M. Halse, and B. Balcom, *Centric Scan SPRITE for spin density imaging of short relaxation time porous materials*, Magn. Reson. Imaging 23, 263 (2005) and Chen, Q., M. Gingras, and B. Balcom, *A magnetic resonance study of pore filling processes during spontaneous imbibition in Berea sandstone*, J. of Chem. Phys. 119, 9609 (2003), which are incorporated herein by reference in their entirety, show that the overall FID (free induction decay) decay rate ($1/T_2^*$) in sedimentary rocks is dominated by an internal field distribution ($\Delta B^i$) induced by the large susceptibility difference ($\Delta_\chi$) between the pore fluid and solid matrix due to paramagnetic impurities in the solid matrix. The decay rate of the FID and the corresponding NMR linewidth ($\Delta v = 1/\pi T_2^*$) for fluid saturated sedimentary rocks may be estimated, as taught in Chen Q., A. Marble, B. Colpitts, and B. Balcom, *The internal magnetic field distribution, and single exponential magnetic resonance free induction decay, in rocks*, J. Magn. Reson. 175, 300 (2005), which is incorporated herein by reference in its entirety, by, $$\frac{1}{\pi T_2^*} = \Delta v \approx \frac{\gamma \Delta B^i}{2\pi} = \frac{C \Delta \chi \gamma B_0}{2\pi} \quad (3)$$

where γ is the gyromagnetic ratio, and $B_0$ is the applied magnetic field strength, while C is a dimensionless constant.

Equation (3) predicts a single exponential $T_2^*$ decay, this prediction has been confirmed by a wide range of MR experiments for sedimentary rocks (see Chen, Q., M. Halse, and B. Balcom, *Centric Scan SPRITE for spin density imaging of short relaxation time porous materials*, Magn. Reson. Imaging 23, 263 (2005); Chen, Q., M. Gingras, and B. Balcom, *A magnetic resonance study of pore filling processes during spontaneous imbibition in Berea sandstone*, J. of Chem. Phys. 119, 9609 (2003); and Chen Q., A. Marble, B. Colpitts, and B. Balcom, *The internal magnetic field distribution, and single exponential magnetic resonance fee induction decay, in rocks*, J. Magn. Reson. 175, 300 (2005), which are incorporated herein by reference in their entirety). Single exponential $T_2^*$ decay is anticipated for a wide variety of sedimentary rock systems, but is not a universal result.

Figure 3:
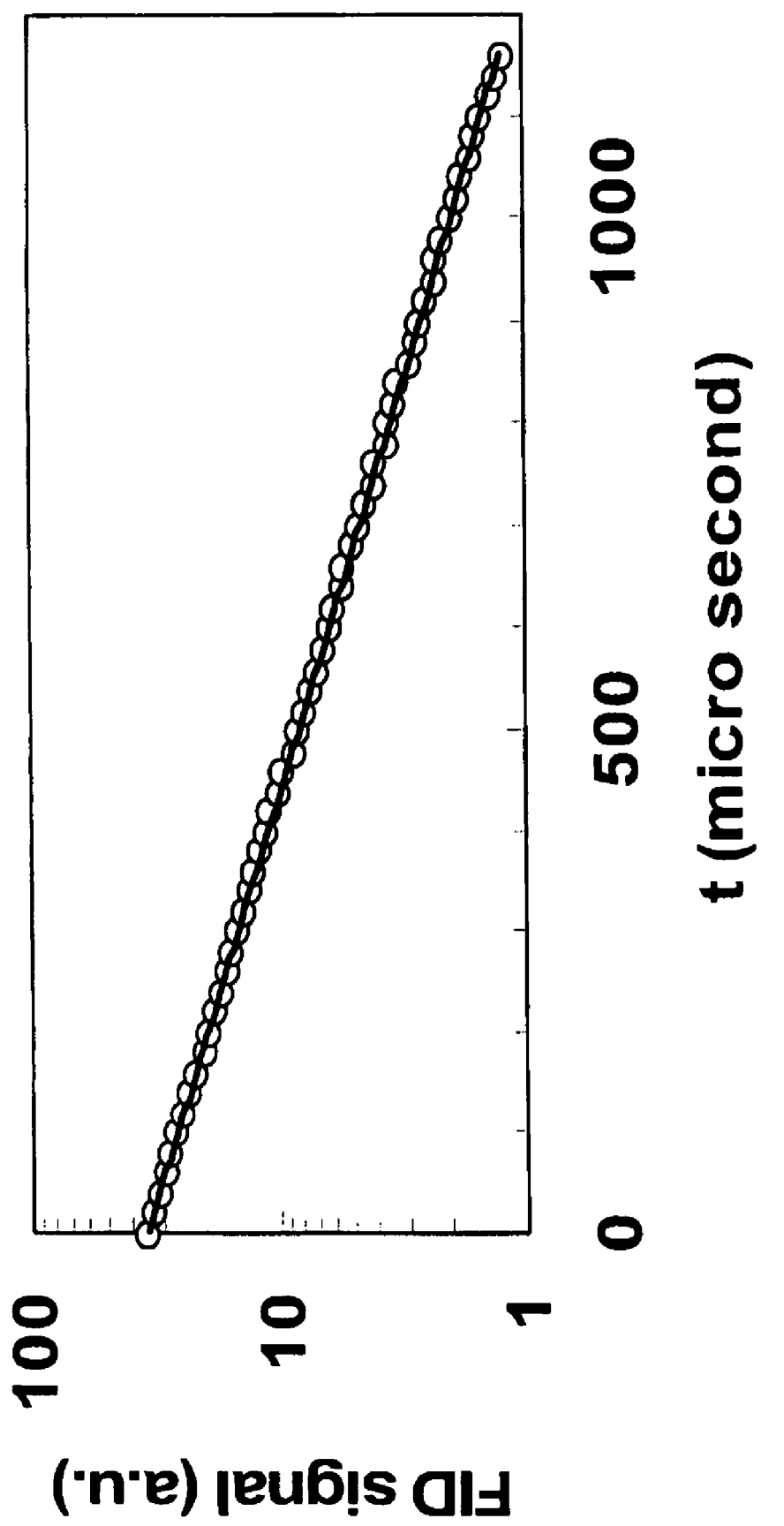
FIG. 3 shows a semi-logarithmical FID decay after a 90 degree RF excitation pulse.

FIG. 3 shows a semi-logarithmical FID decay after a 90 degree RF excitation pulse. FIG. 3 shows a semi-logarithmical plot of the MR FID (free induction decay) of water saturated sandstone. The data was fit to the equation:

$$S = M_0 \exp(-t/T_2^*) \quad (4)$$

where S is the MIR signal intensity, t is the acquisition time. The fit $T_2^*$ was 345 μs. We have observed for many sedimentary rocks that $T_2^*$ is largely insensitive to water saturation with a single exponential FID. These features ensure that Centric Scan SPRITE images are essentially spin density images. Spin density images may not be obtained by spin echo based MRI methods, due to multi-exponential $T_2$ decay in rocks.

Single-Shot Methods

For one-dimensional (e.g. x) steady-state flow, i.e., the fluid saturation and pressure distributions along the length of the core do not change with time, the differential form of Darcy's law may be used to describe multiphase flow in porous media in term of local relationship with relative permeability as a function of local fluid saturation:

$$\frac{Q_j}{A} = -\frac{K K_{rj}}{\mu_j} \frac{dP_j(x)}{dx} \quad (5)$$

where $Q_j$, $P_j(x)$, $\mu_j$, and $K_{rj}$ are volume flux, pressure distribution, viscosity, and relative permeability of fluid phase j, respectively. A, K, and L are the cross-sectional area, absolute permeability and the length of the porous medium, respectively.

Therefore, relative permeability will be determined with Equation 5, if pressure distribution can be obtained.

Capillary Pressure and Relative Permeability Curves Determination of Two-Phase Flow with Gas as One Phase For two-phase flow in porous media, if one phase is gas, gas pressure distribution can be determined by MRI spin density imaging of the gas phase provided MR sensitive gas is employed. Since the gas phase pressure is directly proportional to the spin density of the gas phase.

For steady-state flow, the gas phase mass flow rate, m(x), along the length of the core is constant, and may be expressed by:

$$m = \rho(x) Q(x)/A \quad (6)$$

For an ideal gas:

$$P(x)V(x) = n(x)RT, \text{ or } P(x) = \rho(x)RT/M_w \quad (7)$$

where P(x) is the gas phase pressure distribution along the length (x) of the core, ρ(x) is the gas density distribution along the length (x) of the core, n(x) is mole number of gas phase distribution along the length of the core, R is the idea gas constant, T is the absolute temperature, and $M_w$ is the molecular weight of the gas.

The fluid saturation distribution, S(x), can be obtained by an imaging technique, for example, Centric scan SPRITE MRI.

If the outflow boundary condition (capillary pressure is zero) is maintained by washing the outlet face of the core with oil or water phase. The gas phase pressure distribution, P(x), along the length of the core is equal to the capillary pressure. Therefore, the capillary pressure curve can be determined directly by the combination of P(x) and S(x).

Combination of differential form Darcy's law (Equation 5) with equations 6 and 7 yields a relative permeability of gas phase, $K_{rg}(x)$, along the length of the core, it can be expressed by $$K_{rg}(x) = -\frac{RT\mu(x)m}{KM_w}\left[P(x)\frac{dP(x)}{dx}\right]^{-1} \quad (8)$$

For ideal gases, the local viscosity of the gas μ(x) is independent of gas density, thus μ(x) is constant. Combining $K_{rg}(x)$ with S(x) yields a gas relative permeability curve, $K_{rg}(S)$.

DETAILED STEPS OF ONE EMBODIMENT OF THE METHOD

When a fluid A (water or oil) saturated porous rock core set in a nonmagnetic core holder, is displaced by another fluid B from inlet, while fluid B washes the outlet face of the core to keep 100% saturation of fluid B and zero capillary pressure at outlet. Local fluid saturation may be measured with different techniques, for example Centric scan SPRITE MRI. A steady-state condition is reached, i.e., the fluid saturation and pressure distributions along the length of the core do not change with time.

Figure 4:
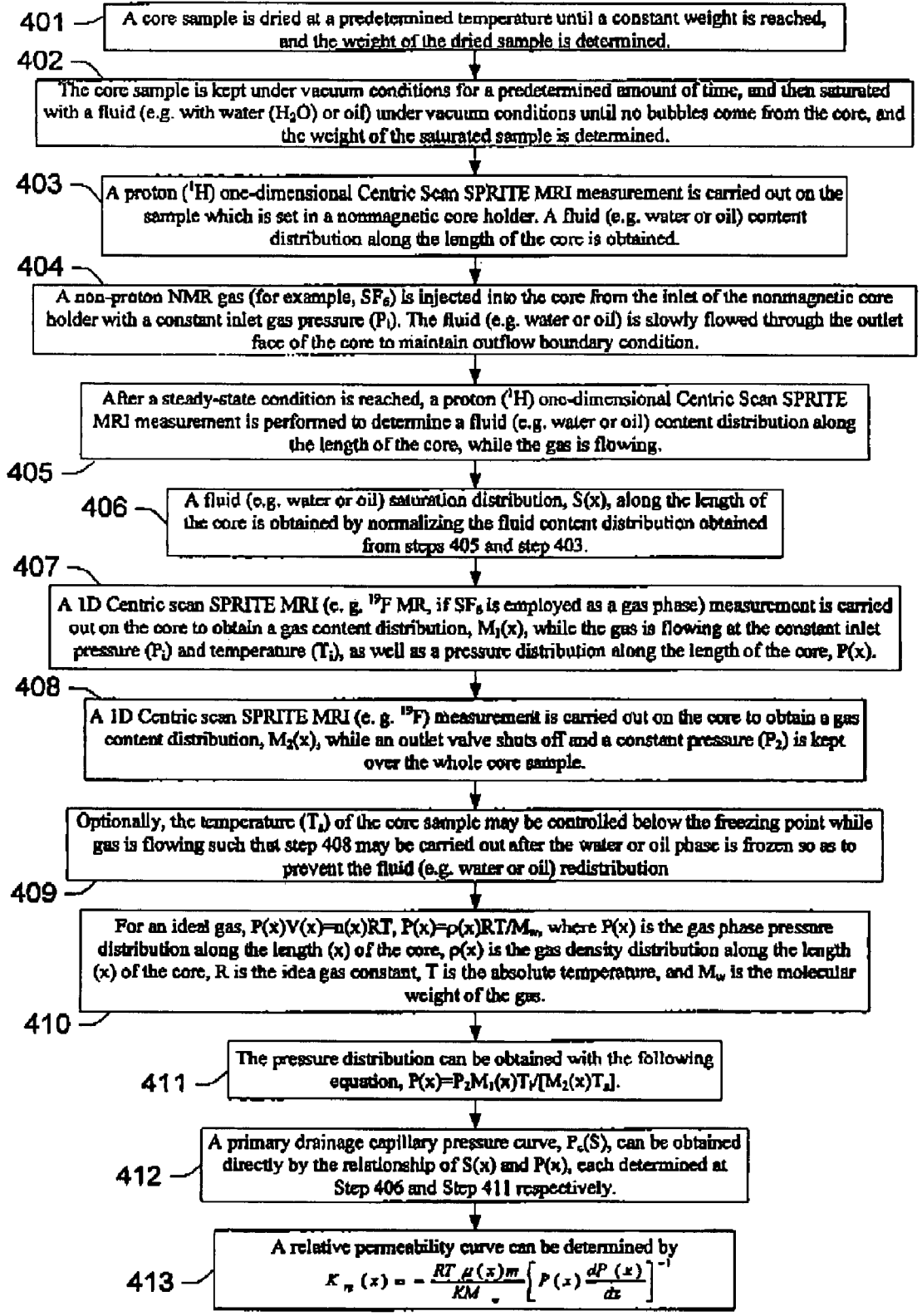
FIG. 4 is a flowchart illustrating steps of one embodiment of a method provided according to the present invention.

Referring to FIG. 4, FIG. 4 is a flowchart illustrating steps of one embodiment of a method provided according to the present invention. Consider a case where water or oil is fluid A, and gas is fluid B, capillary pressure and relative permeability can be obtained by repeating the following manipulative and data processing procedural acts:

1. According to step 401, the cylindrical core sample was dried at 80° C. until a constant weight was reached, and the weight of the dried sample was determined.
2. According to step 402, the core sample was kept under vacuum conditions for more than 24 hours, and then saturated with water ($H_2O$) or oil under vacuum conditions until no bubbles came from the core, and the weight of the saturated sample was determined.
3. According to step 403, a proton ($^1H$) one-dimensional Centric Scan SPRITE MRI measurement was carried out on the sample which is set in a nonmagnetic core holder. A water or oil content distribution along the length of the core was obtained.

4. According to step 404, a non-proton NMR gas (for example, $SF_6$) is injected into the core from the inlet of the nonmagnetic core holder with a constant inlet gas pressure ($P_i$). The water or oil is slowly flow through the outlet face of the core to maintain outflow boundary condition.

5. According to step 405, after the steady-state condition is reached, a proton ($^1H$) one-dimensional Centric Scan SPRITE MRI measurement is performed to determine a water or oil content distribution along the length of the core, while the gas is flowing.

6. According to step 406, a water or oil saturation distribution, $S(x)$, along the length of the core can be obtained by normalizing the fluid content distribution obtained from act 5 and act 3.

7. According to step 407, a 1D Centric scan SPRITE MRI (e.g. $^{19}F$ MR, if $SF_6$ is employed as a gas phase) measurement was carried out on the core to obtain a gas content distribution, $M_1(x)$, while the gas is flowing at the constant inlet pressure ($P_i$) and constant temperature ($T_i$).

8. According to step 408, a 1D Centric scan SPRITE MRI (e.g. $^{19}F$) measurement was carried out on the core to obtain a gas content distribution, $M_2(x)$, while the outlet valve shuts off and a constant pressure ($P_2$) is kept over the whole core sample.

9. According to step 409, to prevent the water or oil redistribution, temperature ($T_s$) of the core sample may be controlled below the freezing point while gas is flowing, act 8 may be carried out after the water or oil phase is frozen.

10. According to step 410, for an idea gas, $P(x)V(x)=n(x)RT$, or $P(x)=\rho(x)RT/M_w$, where $P(x)$ is the gas phase pressure distribution along the length (x) of the core, $\rho(x)$ is the gas density distribution along the length (x) of the core, R is the idea gas constant, T is the absolute temperature, and $M_w$ is the molecular weight of the gas.

11. According to step 411, the pressure distribution can be obtained with the following equation, $P(x)=P_2M_1(x)T_i/[M_2(x)T_s]$.

12. According to step 412, a primary drainage capillary pressure curve, $P_c(S)$, can be obtained directly by the relationship of $S(x)$ and $P(x)$ obtained at acts 6 and 11 respectively.

13. According to step 413, a relative permeability curve can be determined by Equation 8.

In the case that oil or water is flowing phase and gas is stationary phase, the outflow boundary condition is maintained by washing the outlet face of the core with the gas phase, after steady-state condition is reached, the gas phase pressure distribution and flowing water or oil saturation distribution, as well as capillary pressure curve can also be obtained by the similar methods described in the early sections. The gas pressure distribution, $P(x)$, is determined by SPRITE MRI spin density imaging of the stationary gas, while oil or water phase is flowing. The flowing water or oil saturation distribution, $S(x)$, can be measured with SPRITE MRI. The combination of $P(x)$ and $S(X)$ yields a capillary pressure curve, $Pc(S)$ and relative permeability curve of flowing water or oil phase, i.e., $K_{rw}(S)$ or $K_{ro}(S)$ can be determined with differential form of Darcy's law, i.e., Equation 5.

In one embodiment, overburden conditions are applied by maintaining the sample at a representative reservoir pressure during testing. This is accomplished by using a pressurized sample holder which is kept in place during testing.

Relative Permeability Curve Determination of Water and Oil Two-Phase Flow

For oil and water system, the capillary pressure curve, $P_c(S)$, of the core can be determined by other methods, such as, a single-shot centrifuge and MRI method as described in co-pending U.S. patent application Ser. No. 11/262,658 entitled "METHODS AND APPARATUS FOR MEASURING CAPILLARY PRESSURE IN A SAMPLE", filed 31 Oct., 2005 by same inventors (which is hereby incorporated herein by reference in it's entirety), $D_2O$ may be used as the water to distinguish oil from water with MRI. After the single-shot centrifuge experiment, the core is put into a non-magnetic core holder for steady-state flow experiment, the outflow boundary condition is maintained by washing the outlet face of the core with the stationary phase. After the steady-state is reached, water and oil saturation distributions, $S(x)$, along the length of the core can be obtained with Centric scan SPRITE MRI. A combination of $P_c(S)$ and $S(x)$ yields a capillary distribution along the length of the core, $P_c(x)$. The $P_c(X)$ ran be used to determine the flowing phase relative permeability with differential form of Darcy's law, i.e., Equation 5.

In order to eliminate the thermal noise of the MRI spin density imaging, a curve smoothing technique may be applied to smooth the gas pressure distribution curve, $P(x)$, along the length of the core. By thermal noise, random noise in the measurement is included, as all measurements have some degree of random noise. In alternate embodiments, specific smoothing techniques are cubic spline or polynomial interpolation, and many smoothing techniques are possible which would be apparent to a person of ordinary skill in the art. The smoothed curve, $P(x)$, may be used to calculate the relative permeability distribution with equation 5 or 8.

For flowing fluid MRI experiment, the displacement of fluid molecules driven by applied pressure gradient at the period of MRI acquisition ($t_p$) should be maintained to be much smaller than the MRI spatial resolution. The phase encoding time ($t_p$) of SPRITE MRI can be reduced to approximately 30 us, which minimizes the displacement of fluid molecules in the period of the MRI acquisition. If spin echo based MRI is employed, typical minimum echo time is 1 ms, which is too long for the flowing phase MRI (see Bencsik M, and C. Radanathan, Direct measurement of porous media local hydrodynamnic permeability using gas MRI, Magn. Reson. Imaging, 19, 379, 2001, which is incorporated herein by reference in its entirety).

Determination of Required Pressure for Embodiments of the Single-Shot Methods

Embodiments of the single-shot methods require the stationary phase to reach irreducible fluid saturation at inlet face. The inlet pressure for the single-shot methods can be determined by to Leverret (see Leverett M., Capillary behaviour in porous solids, Trans. AIME, 142, 152 (1941), which is incorporated herein by reference in its entirety) J function at irreducible fluid saturation. The Leverett J function is given by:

$$J = \frac{P_c}{\sigma \cos\theta} \sqrt{\frac{k}{\phi}} \quad (9)$$

where $\sigma$ is interfacial tension, $\theta$ is the contact angle, k is permeability, and $\phi$ is porosity.

Reasonable Leverett J values at irreducible water saturation (see Brown H. W., Capillary pressure investigations, Trans. AIME, 192, 67 (1951), which is incorporated herein by reference in its entirety) are $J(S_{wi}) \approx 3-4$.

A linear relationship between gas phase pressure and MR longitudinal relaxation time, $T_1$, may also be used to determined the gas phase pressure distribution, P(x), along the length of the core by measuring the gas phase longitudinal relaxation time distribution, $T_1(x)$, along the length of the core. The measurement of $T_1(x)$ by MRI will be time consuming, therefore spin density imaging of flowing gas phase by 1D Centric scan SPRITE MRI to determine the gas phase pressure distribution along the length of the core will be the primary method. For the spin density MRI measurement with multiple scan to increase signal to noise ratio, a $5T_1$ delay after each single scan is required to eliminate $T_1$ effect on the spin density imaging.

The above-described embodiments of the present invention are intended to be examples only. Those of skill in the art may effect alterations, modifications and variations to the particular embodiments without departing from the scope of the invention, which is set forth in the claims.

What is claimed is:

1. A method suitable for at least enabling the measurement of a property of a porous rock, the method comprising the steps of:
    (a) providing a porous rock core having a length, an inlet face, and an outlet face;
    (b) saturating the porous rock core with a first fluid;
    (c) displacing the first fluid by applying a second fluid to the inlet face of the porous rock core;
    (d) washing the outlet face of the porous rock core with said second fluid so as to maintain an outflow boundary condition;
    (e) determining that a substantially steady-state condition has been reached where the fluid saturation distribution and pressure distribution along the length of the core do not substantially change with time;
    (f) performing a fluid saturation distribution measurement of the porous rock core comprising the act of:
        measuring the local fluid saturation using Nuclear Magnetic Resonance Imaging (NMR) wherein a single exponential free induction decay (FID) rate $1/T_2^*$ is used to provide an NMR linewidth $\Delta v$ is substantially equal to $1/\pi T_2^*$;
    (g) performing a pressure distribution measurement of the porous rock core; and
    (h) determining a property of the porous rock core by using fluid saturation measurement.

2. The method as recited in claim 1, wherein the outflow boundary condition comprises substantially 100% saturation of the second fluid.

3. The method as recited in claim 1, wherein the outflow boundary condition comprises substantially zero capillary pressure at the outlet face or the porous rock core.

4. The method as recited in claim 1, wherein the property of the porous rock determined at said determining step is capillary pressure curve $P_c(S)$ determined by relating P(x) and S(x).

5. The method as recited in claim 1, wherein the property of the porous rock determined at said determining step is relative permeability determined by applying a differential form of Darcy's law and ideal gas equations for gas flowing at steady-state.

6. The method as recited in claim 1, further comprising the step of:
    setting the porous rock core in a nonmagnetic core holder.

7. The method as recited in claim 6, wherein the first fluid is a liquid, and wherein the second fluid is gas.

8. The method as recited in claim 7, wherein the liquid is water.

9. The method as recited in claim 7, wherein the liquid is oil.

10. The method as recited in claim 7, further comprising the step of, prior to the step of saturating the porous rock core, drying the porous rock core until a constant weight is reached.

11. The method as recited in claim 10, wherein the step of drying the porous rock core comprises the act of drying at substantially 80° C.

12. The method as recited in claim 7, further comprising the step of determining the weight of the porous rock core prior to the saturating step.

13. The method as recited in claim 7, further comprising the step of keeping the porous rock core under vacuum conditions.

14. The method as recited in claim 13, wherein the step of keeping the porous rock core under vacuum is performed for more than 24 hours.

15. The method as recited in claim 13, wherein the step of saturating further comprises the act of saturating with the liquid under vacuum conditions until no bubbles come from the porous rock core.

16. The method as recited in claim 15, further comprising the step of, after the saturating step, determining the weight of the saturated porous rock core.

17. The method as recited in claim 6, wherein the step of performing a fluid saturation measurement comprises the act of carrying out a proton ($^1$H) one-dimensional Centric Scan SPRITE MRI measurement on the porous rock core set in the nonmagnetic core holder.

18. The method as recited in claim 17, wherein the step of determining a property of the porous rock core by using the measurement comprises the act of obtaining a liquid content distribution along the length of the porous rock core.

19. The method as recited in claim 6, wherein the step of forming fluid saturation measurement comprises the act of carrying out a fluorine centric scan SPRITE MRI measurement on the porous rock core set in the non-magnetic core holder.

20. The method as recited in claim 7, wherein the gas is a non-proton NMR gas.

21. The method as recited in claim 20, wherein the non-proton NMR gas is $SF_6$.

22. The method as recited in claim 7, wherein the step of displacing the first fluid comprises the act of injecting the gas into the porous rock core from the inlet of the nonmagnetic core holder with a constant inlet gas pressure ($P_i$).

23. The method as recited in claim 7, wherein the step of washing the outlet face of the porous rock core comprises the act of flowing the liquid slowly though the outlet face of the porous rock core, so as to substantially maintain the outflow boundary condition.

24. The method as recited in claim 17, wherein the act of carrying out a first proton ($^1$H) one-dimensional Centric Scan SPRITE MRI measurement is performed prior to the step of displacing the first fluid.

25. The method as recited in claim 24, wherein the act of carrying out a second proton ($^1$H) one-dimensional Centric Scan SPRITE MRI measurement is performed after the steady-state condition is reached while the second fluid is flowing at the present of the first fluid remaining stationary.

26. The method as recited in claim 24, wherein the step of performing a fluid saturation measurement further comprises the act of carrying out a first proton ($^1$H) one-dimensional Centric Scan SPRITE MRI measurement on the porous rock core set in the nonmagnetic core holder prior to the step of displacing the first fluid.

27. The method as recited in claim 25, wherein the act of carrying out a second proton ($^1$H) one-dimensional Centric Scan SPRITE MRI measurement is performed contemporaneously with the step of displacing the first fluid.

28. The method as recited in claim 25, wherein the step of determining the property of the porous rock core by using the fluid saturation measurement comprises the act of normalizing a first NMR measurement using a second NMR measurement.

29. The method as recited in claim 28, wherein one of the first and second NMR measure is on the porous rock core.

30. The method as recited in claim 29, wherein the other of the first and second NMR measurement is on the porous rock core.

31. The method as recited in claim 29, wherein the other of the first and second NMR measurement is on a standard sample which does not comprise the porous rock core.

32. The method as recited in claim 31, wherein the standard sample is water.

33. The method as recited in claim 31, wherein the standard sample NMR is measured less frequently than the rock core NMR for calibration thereby further increasing the speed of the property determining step.

34. The method as recited in claim 28, wherein the property of the porous rock core, in the step of determining a property of the porous rock core by using the fluid saturation measurement, is liquid saturation distribution S(x) along the length of the porous rock core.

35. The method as recited in claim 7, further comprising the step of carrying out a 1D Centric scan SPRITE MRI measurement on the porous rock core.

36. The method as recited in claim 35, further comprising the step of obtaining a gas content distribution $M_1(x)$ along the length of the porous rock core using the 1D Centric scan SPRITE MRI measurement on the porous rock core.

37. The method as recited in claim 36, wherein the step of carrying out a 1D Centric scan SPRITE MRI measurement on the porous rock core is performed while the gas is flowing at a constant inlet pressure ($P_i$).

38. The method as recited in claim 36, wherein the step of carrying out a 1D Centric scan SPRITE ME measurement on the porous rock core is performed while the gas is flowing at a constant Temperature ($T_i$).

39. The method as recited in claim 35, further comprising the step of obtaining a pressure distribution P(x) along the length of the porous rock core using the 1D Centric scan SPRITE MRI measurement on the porous rock core.

40. The method as recited in claim 35, wherein the gas is $SF_6$ and wherein the step of carrying out a 1D Centric scan SPRITE MRI measurement on the porous rock core includes employing $^{19}$F MR.

41. The method as recited in claim 36, further comprising the step of obtaining a gas content distribution, $M_2(x)$ along the length of the porous rock core using the 1D Centric scan SPRITE MRI measurement on the porous rock core.

42. The method as recited in claim 41, wherein the step of carrying out 1D Centric scan SPRITE MRI measurement on the porous rock core is performed while an outlet valve shuts off.

43. The method as recited in claim 41, wherein the step of carrying out 1D Centric scan SPRITE MRI measurement on the porous rock core is performed while a constant pressure ($P_2$) is kept over the whole porous rock core.

44. The method as recited in claim 43, further comprising the step of controlling the temperature ($T_s$) of the porous core rock below the liquid freezing point while gas is flowing so as to prevent the liquid from redistribution.

45. The method as recited in claim 44, wherein the step of carrying out 1D Centric scan SPRITE MRI measurement on the porous rock core is carried out after the liquid is frozen.

46. The method as recited in claim 44, further comprising the step of obtaining the pressure distribution with the following equation $P(x)=P_2 M_1(x) T_i/[M_2(x)T_s]$.

47. The method as recited in claim 46, wherein the property of the porous rock core, in the step of determining a property of the porous rock core by using the fluid saturation measurement, is gas pressure saturation distribution P(x) along the length of the porous rock core.

48. The method as recited in claim 47, further comprising the step of obtaining a primary drainage capillary pressure curve $P_c(S)$ by relating S(x) and P(x).

49. The method as recited in claim 48, further comprising the step of determining a relative permeability of gas $K_{rg}(x) = -[RT\mu(x)m/KM_w][P(x)dP(x)/dx]^{-1}$, where R is the ideal gas constant, T is the absolute temperature of the gas, $\mu(x)$ is the local viscosity of the flowing gas which can be a constant that is independent of gas density for an ideal gas, m is the mass flow rate of the gas, K is the absolute permeability, and $M_w$, is the molecular weight of the gas.

50. The method as recited in claim 49, further comprising the step of combining $K_{rg}(x)$ with S(x) to obtain a relative permeability curve $K_{rg}(S)$.

51. The method as recited in claim 7, further comprising the step of keeping the porous rock core at overburden conditions.

52. The method as recited in claim 51, wherein the step of keeping the porous rock core at overburden conditions is performed more than 24 hours.

53. The method as recited in claim 51, wherein the overburden condition is at elevated temperature.

54. The method as recited in claim 51, wherein the overburden condition is at elevated pressure.

55. The method as recited in claim 1, wherein the FID rate is dominated by an internal field distribution $\Delta B^i$.

56. The method as recited in claim 55, wherein the internal field distribution $\Delta B^i$ is induced by a susceptibility difference $\Delta_\chi$ between at least one of the first fluid and second fluid and the porous rock core.

57. The method as recited in claim 56, wherein the susceptibility difference $\Delta_\chi$ is due to paramagnetic impurities in the porous rock core.

58. The method as recited in claim 1, wherein the NMR uses the technique of centric scan Single-Point Ramped Imaging with $T_1$ Enhancement (SPRITE) Magnetic Resonance Imaging (MRI).

59. The method as recited in claim 1, wherein the NMR uses a double half k-space acquisition strategy.

60. The method as recited in claim 1, wherein the fluid saturation measurement step is a single-shot measurement so as to increase speed of the determining step.

61. The method as recited in claim 1, wherein the fluid saturation measurement step is not single-shot so as to increase resolution of the determining step.

62. A method suitable for determining capillary pressure and relative permeability curves of a porous rock core having an inlet face and an outlet face, the method comprising the steps of:
(a) maintaining a steady-state gas flow, with stationary water or oil remaining in a porous rock core;
(b) maintaining an outflow boundary condition whereat capillary pressure is zero by washing the outlet face of the core with a stationary phase;

(c) measuring a water or oil saturation distribution, S(x), at the present of steady-state flowing gas, using MRI; and (d) determining a gas pressure distribution, P(x), by SPRITE (Single-Point Ramped Imaging with T1 Enhancement) MIR (Magnetic Resonance Imaging) spin density imaging of flowing gas, whereby the pressure of the gas phase is directly proportional to the spin density of gas.

63. The method as recited in claim 62, further comprising the step of combining P(x) and S(x) to yield a capillary pressure curve, $P_c(S)$.

64. The method as recited in claim 62, further comprising the step of obtaining a relative permeability curve of flowing gas phase, $K_{rg}(S)$ by using a differential form of Darcy's law and ideal gas equations for gas flowing at steady-state.

* * * * *